United States Patent [19]
Chiang et al.

[11] Patent Number: 5,806,666
[45] Date of Patent: Sep. 15, 1998

[54] DENTAL FLOSS CONTAINER

[75] Inventors: Casper W. Chiang, Danville; Edgardo G. Zapanta, San Bruno, both of Calif.

[73] Assignee: Gillette Canada Inc., Kirkland, Canada

[21] Appl. No.: 878,432

[22] Filed: Jun. 18, 1997

[51] Int. Cl.⁶ .................................................. A61C 15/04
[52] U.S. Cl. ..................... 206/63.5; 206/409; 132/325; 225/47; 225/89
[58] Field of Search .................... 206/63.5, 408, 206/409, 368, 397; 132/309, 323–325, 329; 225/39, 47, 56, 89, 34

[56] References Cited

U.S. PATENT DOCUMENTS

| | | |
|---|---|---|
| D. 180,981 | 9/1957 | Williams . |
| D. 189,548 | 1/1961 | Gershen . |
| D. 192,007 | 1/1962 | Gershen . |
| D. 256,999 | 9/1980 | Haagedoorn et al. . |
| D. 271,431 | 11/1983 | Seelig . |
| D. 295,020 | 4/1988 | Franchi . |
| D. 341,909 | 11/1993 | Schneider . |
| 1,050,560 | 1/1913 | Moore . |
| 2,145,178 | 1/1939 | Hawkins . |
| 2,550,944 | 5/1951 | Stack . |
| 2,929,541 | 3/1960 | Castelli et al. . |
| 2,944,761 | 7/1960 | Best . |
| 2,967,651 | 1/1961 | Zackheim et al. . |
| 3,106,363 | 10/1963 | Epstein . |
| 3,246,815 | 4/1966 | Aronson . |
| 3,270,980 | 9/1966 | Philips . |
| 3,312,410 | 4/1967 | Strothmann . |
| 3,502,281 | 3/1970 | McLain . |
| 3,734,107 | 5/1973 | Theirman . |
| 3,746,225 | 7/1973 | Runckel ................................. 225/56 |
| 3,901,251 | 8/1975 | Johnston . |
| 4,016,892 | 4/1977 | Chodorow . |
| 4,050,648 | 9/1977 | Tisma . |
| 4,073,419 | 2/1978 | Tarrson et al. . |
| 4,141,519 | 2/1979 | Tarrson et al. . |
| 4,142,538 | 3/1979 | Thornton . |
| 4,169,688 | 10/1979 | Toshio . |
| 4,231,381 | 11/1980 | Battista . |
| 4,327,755 | 5/1982 | Endelson . |
| 4,635,660 | 1/1987 | Graves . |
| 4,657,034 | 4/1987 | Koski . |
| 4,796,783 | 1/1989 | Paulson ................................... 206/409 |
| 4,881,560 | 11/1989 | Blank et al. . |
| 4,925,073 | 5/1990 | Tarrson et al. . |
| 4,934,389 | 6/1990 | Pettiford . |
| 4,944,440 | 7/1990 | Fortman . |
| 4,974,614 | 12/1990 | Selker . |
| 5,022,577 | 6/1991 | Fike ......................................... 225/39 |
| 5,065,861 | 11/1991 | Greene et al. . |
| 5,076,302 | 12/1991 | Chari . |
| 5,076,423 | 12/1991 | Russack . |
| 5,086,792 | 2/1992 | Chodorow . |
| 5,156,311 | 10/1992 | Spencer, Jr. et al. ..................... 225/47 |
| 5,160,077 | 11/1992 | Sticklin ................................... 225/47 |
| 5,282,563 | 2/1994 | Oliver et al. . |
| 5,299,723 | 4/1994 | Hempel . |
| 5,566,872 | 10/1996 | Dolan et al. ............................. 225/47 |
| 5,570,710 | 11/1996 | Wei et al. . |
| 5,573,021 | 11/1996 | Grofcisk et al. . |
| 5,607,050 | 3/1997 | Dolan et al. ........................... 206/63.5 |

*Primary Examiner*—Paul T. Sewell
*Assistant Examiner*—Luan K. Bui
*Attorney, Agent, or Firm*—Fish & Richardson P.C.

[57] ABSTRACT

A dental floss dispenser is provided comprising a molded plastic housing which may be disassembled by the user to change the position of a removable cutting edge for the floss to one of two mounting positions within the housing. When the cutting edge is mounted in one mounting position, the dispensing and cutting of the thread is convenient for a right-handed user and when it is mounted in the other mounting position, the dispensing and cutting of the floss is convenient for a left-handed user.

7 Claims, 3 Drawing Sheets

DENTAL FLOSS CONTAINER

The present invention is directed to a dental floss dispenser. More specifically, the invention is directed to a dental floss dispenser capable of being readily converted to convenient use by left-handed or right-handed users.

BACKGROUND OF THE INVENTION

Dental floss dispensers for home use typically incorporate a body of plastic capable of being held in one hand from which the floss is unreeled, and a cutting edge, typically a metal detente, through which the floss is wedged for cutting by the user. Typically, the dispenser is held in one hand and the floss is pulled out to an appropriate length with the other hand, wedged into the cutter and pulled to cut the floss. Since most users are right-handed, the dispenser is typically designed so the floss may be unreeled to the right side of the dispenser while held in the left hand and the cutting edge is disposed so that the floss is cut by a pulling motion using the right hand.

There is usually also a cover to protect the dispensing orifice and the cutting edge when not in use. While there are different ways to locate the cover with respect to the cutting edge, in many instances, the cover is disposed with respect to the cutting edge so as to make dispensing and cutting of the floss most convenient to a right-handed person.

The present invention is directed to a novel dental floss dispenser which can be readily adapted by the user for convenience of use by either a left-handed or a right-handed person.

SUMMARY OF THE INVENTION

An apparatus is disclosed for holding, containing and dispensing sterile, hygienic cordage, such as dental floss. The apparatus comprises a housing having first and second mounting receptacles for removably receiving a cutting device for cutting the cordage. The apparatus further comprises at least one dispensing orifice disposed adjacent to the cutting device such that the cordage can be fed from the dispensing orifice to the cutting device cut by the user by gripping the housing with one hand, gripping the cordage with the other hand and pulling the cordage against the cutting edge of the cutting device. The apparatus also comprises a retaining spool for retaining the cordage within the apparatus.

A second mounting receptacle on the apparatus on which the cutting device is not mounted is also disposed adjacent to a dispensing orifice such that the cutting device may be removed from the first mounting receptacle to the second mounting receptacle. When the cutting device is mounted on the first mounting receptacle, the cordage will be more conveniently and facilely dispensed and cut by the user holding the cordage in the right hand. The mounting of the cutting device on the second mounting receptacle will make it more convenient and facile for the user to dispense and cut the cordage using the left hand.

DESCRIPTION OF THE PREFERRED EMBODIMENTS

A dental floss dispenser is disclosed comprising a housing, which may be formed of molded plastic parts, containing a spool upon which the dental floss may be wound for storage and retention.

Figure 1:
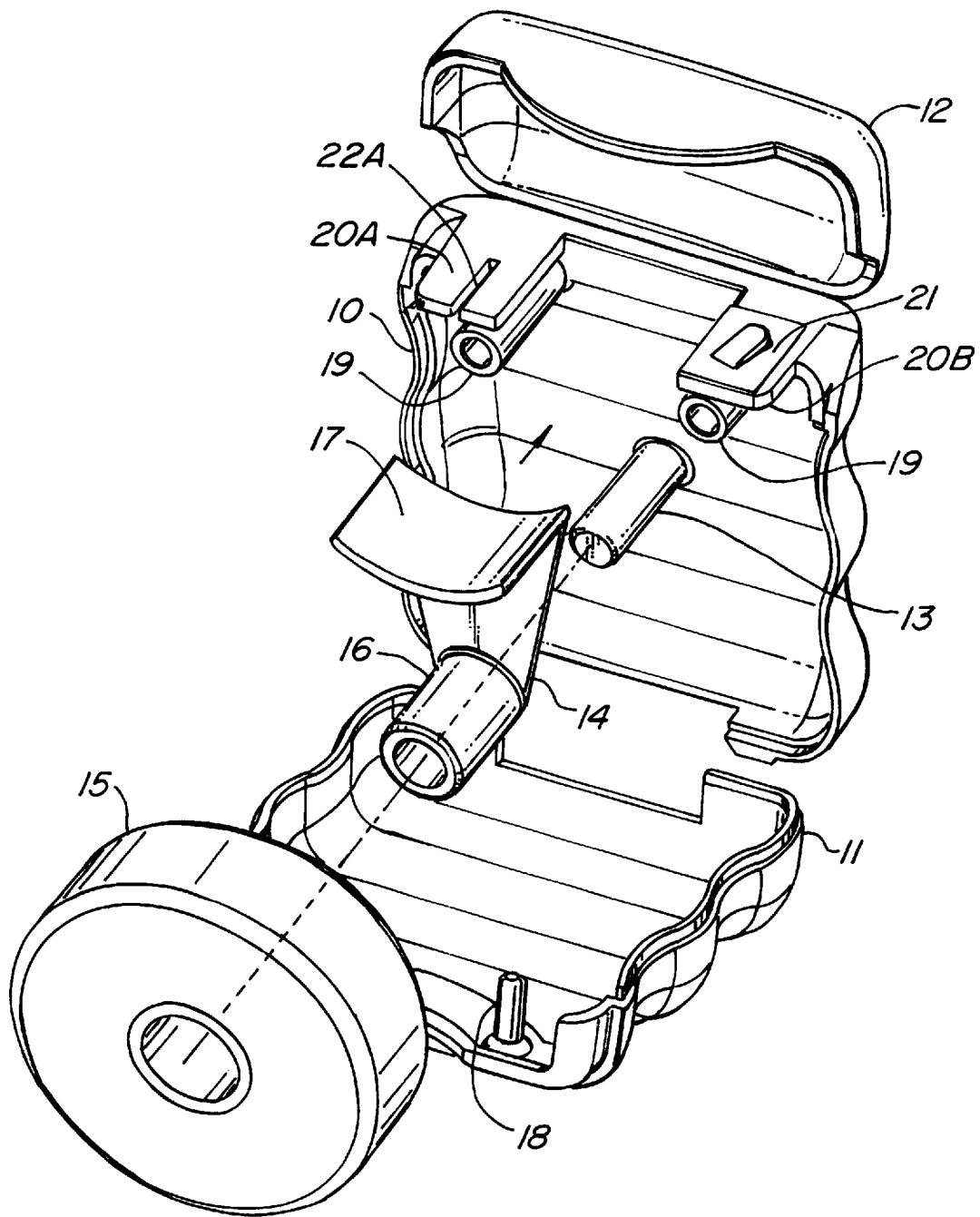
FIG. 1 is an exploded view a preferred embodiment of the dental floss dispenser according to the present invention.

Referring to FIG. 1, there is disclosed a plastic housing comprising two major portions, one forming the back section 10 and one forming the front section 11. The back section 10 also has hinged to it a cover 12 which is molded to the back section 10 and connected thereto so it is flexible at the point of attachment. Molded on the internal portion of the back section 10 is a circular stem 13 for receiving the spool holder 14 which is a separate article. The spool 15 will retain the dental floss and be retained on the spool holder stem 16. The spool holder 14 also preferably has a portion thereof 17 which may be made of a clear plastic which allows the user to view the spool 15 within the housing and the remaining amount of floss on the spool.

The portions 10 and 11 are adapted to fit together by a plurality of tabs 18 and tab receptacles 19 which can be snapped together or otherwise securely held. On the back portion 10 of the housing, there are two slotted tabs 20A and 20B, with a metal cutting detente 21 shown as being affixed to receptacle 20B. Each of the receptacles 20A and 20B (obscured by detente 21) is also provided with slots 22A and 22B, respectively, through which the floss is dispensed from the internal area of the apparatus for use.

Figure 2:
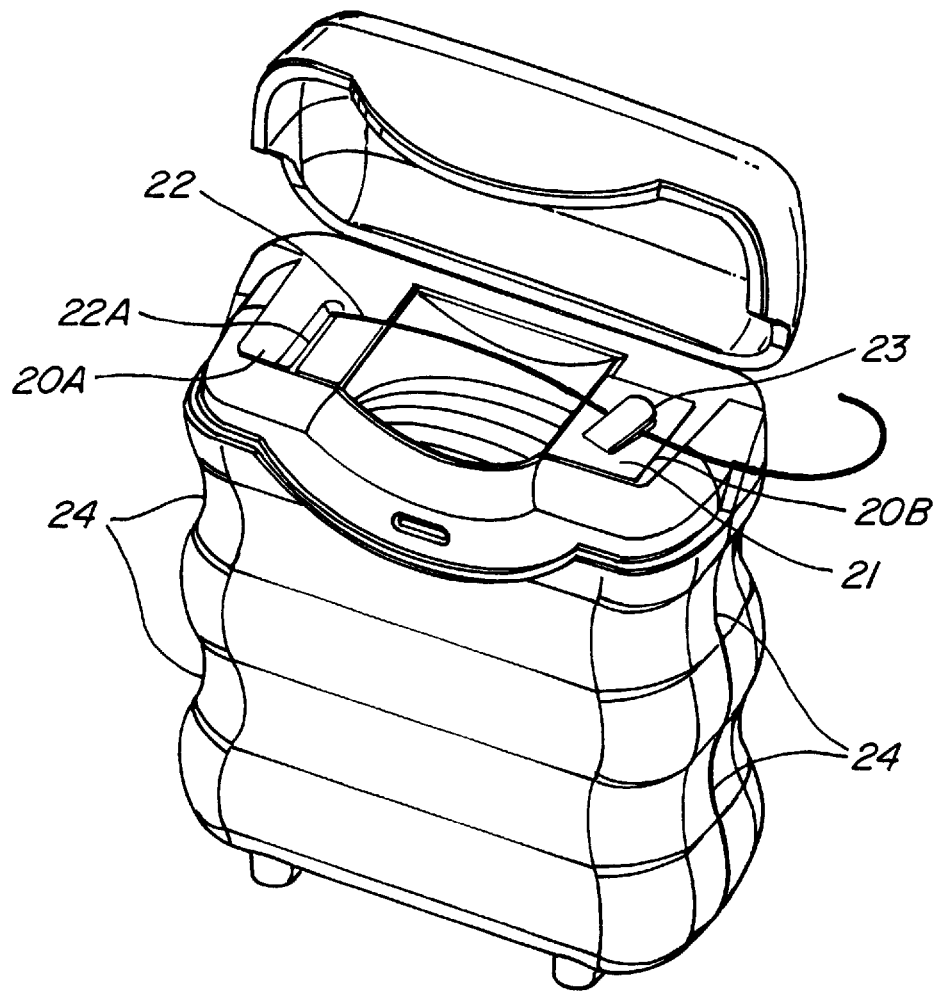
FIG. 2 is a perspective view of the preferred embodiment of FIG. 1, showing the cutting edge disposed for the convenience of a right-handed user.

Referring to FIG. 2, there is shown an assembled dental floss dispenser according to FIG. 1 with the metal cutter detente 21 removably attached to receptacle 20B. As shown in FIG. 2, the floss 22 exits from the internal area of the apparatus through slot 22A and is threaded through the cutting edge 23 of the cutting detente 21. The slot 22A is disposed so that the cutting edge 23 is in alignment with it to receive the floss against the cutting edge. As assembled, the apparatus has indentations 24 for the fingers for convenient gripping of the body of the apparatus as shown in FIG. 2. It is most convenient for the user to hold the apparatus in the left hand with the cover opened toward the side facing away from the user as shown in FIG. 2. The floss 22 within the apparatus is drawn to a desired length and pulled toward the user with the right hand against the cutting edge 23 to cut the floss.

Figure 3:
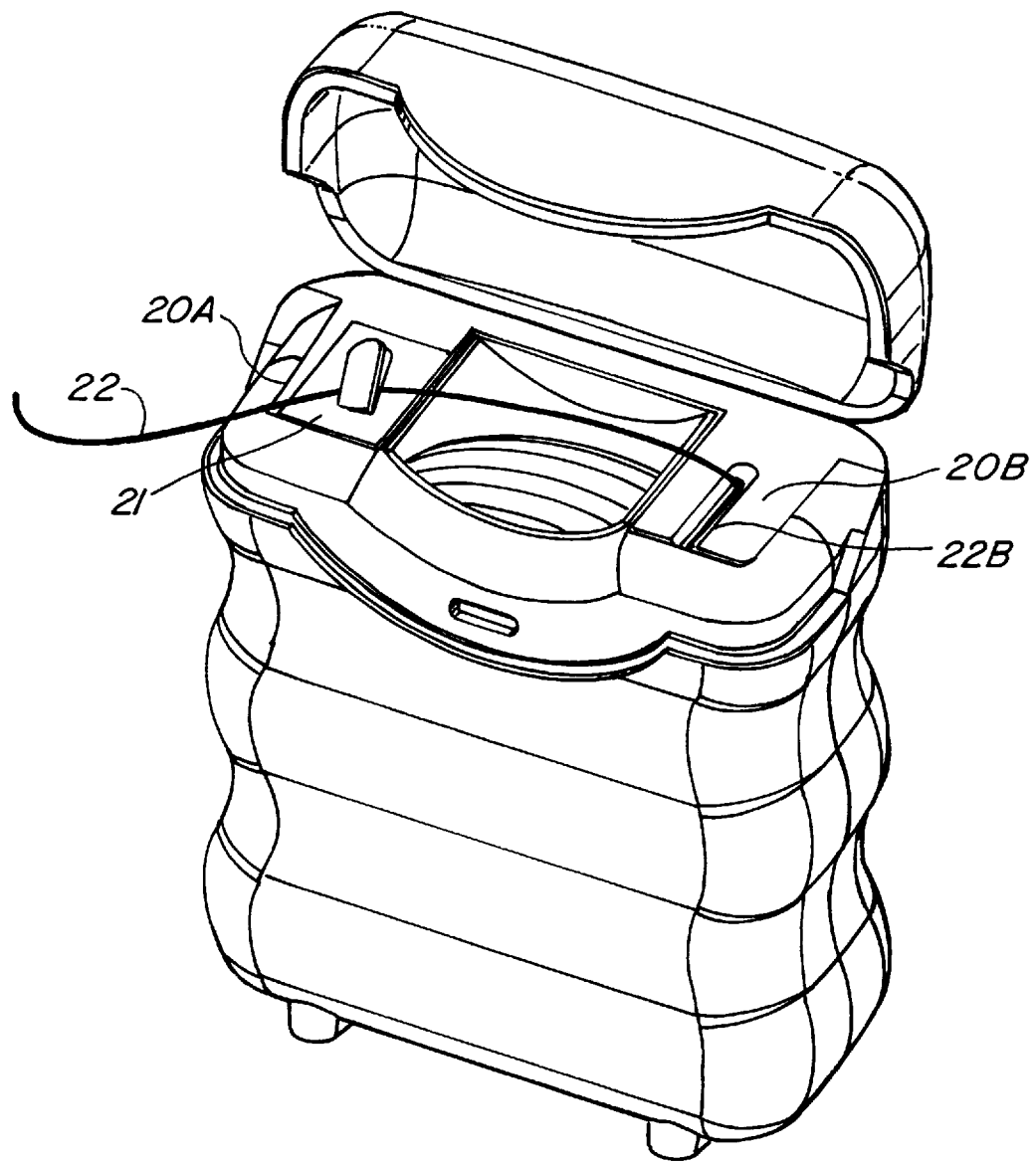
FIG. 3 is a perspective view of the embodiment of FIG. 1, with the cutting edge disposed for the convenience of a left-handed user.

Referring to FIG. 3, there is shown the apparatus according to FIG. 1 with the metal cutting detente 21 now attached to the alternate receptacle 20A. In this configuration, the user will grip the apparatus in the right hand and withdraw and cut the floss by pulling towards the user using the left hand.

The body of the apparatus may be readily disassembled by way of the tabs 18 and tab receptacles 19 so that the cutting device may be removably mounted to either receptacle 20A or 20B, at the option of the user.

A particular advantage of the dental floss dispenser is the ability of the user to adapt the mode of dispensing and cutting the floss for the convenience of the left-handed or right-handed person. In addition, the presence of the transparent window which is viewable when the cover is raised, allows the user to determine the amount of dental floss remaining on the spool without fully disassembling the dispenser.

While the invention has been disclosed herein, along with a detailed description of embodiments, it will be clear to those skilled in the art that modifications or variations of such details can be made without deviating from the essence of the invention and such modifications or variations are considered to be within the scope of the appended claims.

What is claimed is:

1. An apparatus for holding, containing and dispensing sterile, hygienic cordage comprising:
   a) a housing having a first and second mounting means;
   b) cutting means removably mounted to said first mounting means;
   c) retaining means for containing and storing said cordage within said apparatus;
   d) at least one dispensing orifice for withdrawing the cordage from said apparatus for use;
   wherein said dispensing orifice is disposed adjacent to said cutting means mounted on said first mounting means such that said cordage can be fed from said retaining means through said dispensing orifice to said cutting means and said cordage can be cut by the user by gripping said housing with the left hand, gripping said cordage with the right hand and pulling said cordage against said cutting means to cut said cordage;
   and wherein said second mounting means is disposed such that said cutting means can be removably mounted thereon and said housing can be held with the right hand, said cordage can be gripped with the left hand, withdrawn and pulled against the cutting edge with the left hand to cut said cordage.

2. An apparatus according to claim 1 further comprising a removable cover for protecting said dispensing means and cutting means when not in use.

3. An apparatus according to claim 1 wherein said retaining means comprises a spool for accommodating said cordage, an axle for receiving said spool and a transparent window for viewing the cordage remaining on said spool.

4. An apparatus according to claim 1 wherein said housing contains indentations for gripping said housing.

5. An apparatus according to claim 1 wherein said first and second mounting means each comprises a tab, and said cutting means comprises a metallic cutting edge and bracket, said bracket being adapted to receive either of said tabs in a position to present said cutting edge in alignment with said dispensing means for receiving said cordage.

6. An apparatus according to claim 1 wherein said dispensing orifice comprises a slot in said second mounting means.

7. An apparatus according to claim 6 further comprising a second dispensing orifice which comprises a slot in said first mounting means.

* * * * *